US012594218B1

(12) United States Patent
Wilt et al.

(10) Patent No.: US 12,594,218 B1
(45) Date of Patent: Apr. 7, 2026

(54) BENDABLE THERAPEUTIC DEVICE FOR TISSUE DISCOMFORT RELIEF

(71) Applicant: Plus EV Holdings Inc., North Kansas City, MO (US)

(72) Inventors: Aaron R. Wilt, North Kansas City, MO (US); Amanda A. Olson, Medford, OR (US); Jinchen Li, Overland Park, KS (US)

(73) Assignee: Plus EV Holdings Inc., Kansas City, MO (US)

( * ) Notice: Subject to any disclaimer, the term of this patent is extended or adjusted under 35 U.S.C. 154(b) by 0 days.

(21) Appl. No.: 19/005,687

(22) Filed: Dec. 30, 2024

(51) Int. Cl.
| | |
|---|---|
| *A61H 39/04* | (2006.01) |
| *A61H 21/00* | (2006.01) |
| *A61H 23/02* | (2006.01) |
| *A61N 5/06* | (2006.01) |

(52) U.S. Cl.
CPC ......... *A61H 23/0254* (2013.01); *A61H 21/00* (2013.01); *A61N 5/0616* (2013.01); *A61H 2201/0192* (2013.01); *A61H 2201/0207* (2013.01); *A61H 2201/0214* (2013.01); *A61H 2201/10* (2013.01); *A61N 2005/0663* (2013.01)

(58) Field of Classification Search
CPC .......... A61H 7/00; A61H 7/001; A61H 7/002; A61H 7/003; A61H 7/005; A61H 39/00; A61H 39/04; A61H 39/06; A61H 19/00; A61H 19/40; A61H 19/44
See application file for complete search history.

(56) References Cited

U.S. PATENT DOCUMENTS

| | | | | |
|---|---|---|---|---|
| 750,735 | A * | 1/1904 | Turck | A61H 23/0263 601/72 |
| 2,478,786 | A * | 8/1949 | Smallen | A61H 21/00 601/137 |
| 4,002,164 | A * | 1/1977 | Bradley | A61H 21/00 601/134 |
| 4,878,489 | A * | 11/1989 | Kamayachi | A61H 23/0263 601/72 |
| 5,697,966 | A * | 12/1997 | Boutos | A61N 1/0452 607/138 |
| 7,695,489 | B2 * | 4/2010 | Brockman | A61N 5/045 482/121 |
| 8,622,890 | B1 * | 1/2014 | Caggiano | A61H 19/50 600/38 |

(Continued)

OTHER PUBLICATIONS

Newflora, "Pelvic and Perineal Massage Wand", retrieved from <https://newflora. com/products/pelvic-wands> on Jul. 17, 2025, 7 pages.

(Continued)

*Primary Examiner* — Justine R Yu
*Assistant Examiner* — Christopher E Miller
(74) *Attorney, Agent, or Firm* — Workman Nydegger

(57) ABSTRACT

An apparatus for tissue trigger point therapy is disclosed. The apparatus includes an elongated core that includes a bendable portion, a first end portion forming a first terminal end of the elongated core, and a second end portion forming a second terminal end of the elongated core. The apparatus also includes an outer covering member that at least partially surrounds the elongated core and that is also bendable with the bendable portion of the elongated core.

19 Claims, 6 Drawing Sheets

(56) References Cited

U.S. PATENT DOCUMENTS

| | | | | |
|---|---|---|---|---|
| 2003/0009116 A1* | 1/2003 | Luettgen | A61H 19/34 | 601/72 |
| 2004/0267173 A1* | 12/2004 | Mangano | A61H 11/00 | 601/57 |
| 2005/0130818 A1* | 6/2005 | Karol | A63B 23/20 | 482/148 |
| 2005/0273024 A1* | 12/2005 | Nan | A61H 19/44 | 600/38 |
| 2008/0009775 A1* | 1/2008 | Murison | A61H 19/44 | 600/38 |
| 2008/0281345 A1* | 11/2008 | Wise | A61N 1/0512 | 606/191 |
| 2010/0076257 A1* | 3/2010 | DeAlva | A61H 19/40 | 600/38 |
| 2014/0088469 A1* | 3/2014 | Wise | A61N 1/0512 | 601/46 |
| 2014/0228628 A1* | 8/2014 | De Alva | A61H 19/44 | 600/38 |
| 2018/0104460 A1* | 4/2018 | Peters | A61M 29/00 | |
| 2019/0060162 A1* | 2/2019 | Martin | A61H 19/34 | |
| 2021/0022949 A1* | 1/2021 | Janapol | A61H 23/0263 | |
| 2021/0030620 A1* | 2/2021 | Wilt | A61H 19/44 | |
| 2021/0283006 A1* | 9/2021 | Bolton | A61H 19/44 | |
| 2023/0310262 A1* | 10/2023 | Crozier | A61H 19/50 | 600/38 |
| 2024/0299242 A1* | 9/2024 | Harris | A61H 23/006 | |

OTHER PUBLICATIONS

Newflora, "Vibrating Pelvic and Perineal Massage Wand", retrieved from <https://newflora.com/products/vibrating-pelvic-wand> on Jul. 17, 2025, 9 pages.

Complaint for Design Patent Infringement from U.S. Pat. No. D. 1,029,286, filed by Plus EV Holdings, Inc. on Aug. 1, 2024, 9 pages.

Answer to Complaint and Counterclaims from U.S. Pat. No. D. 1,029,286, filed by NewFlora on Nov. 4, 2024, 33 pages.

First Amended Answer and Counterclaims from U.S. Pat. No. D. 1,029,286, filed by NewFlora on Dec. 27, 2024, 116 pages.

Answer to Intimate Rose's 12(c) Motion from U.S. Pat. No. D. 1,029,286, filed by Plus EV Holdings, Inc. on Jan. 3, 2025, 30 pages.

* cited by examiner

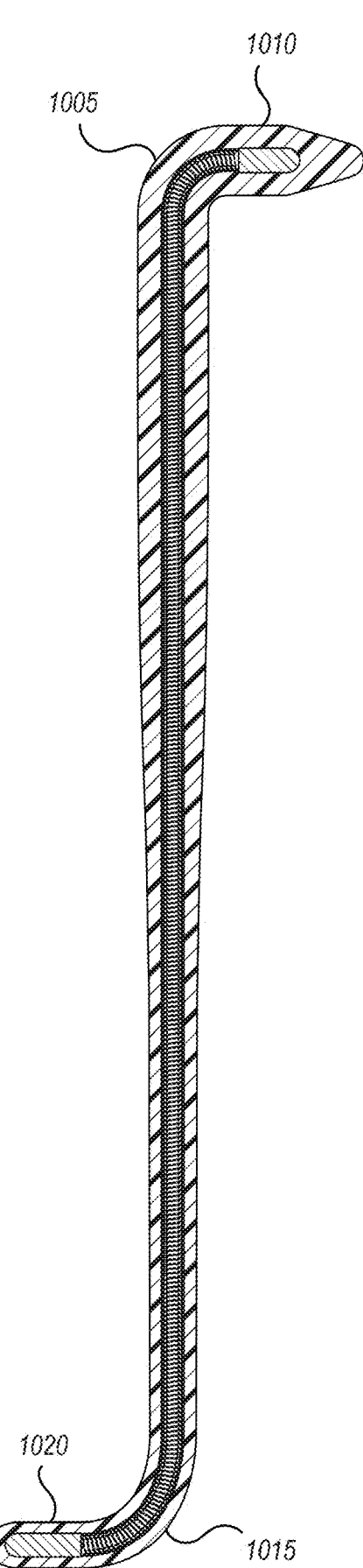
_1000_
_1005_    _1010_
_1020_    _1015_
_FIG. 10_

BENDABLE THERAPEUTIC DEVICE FOR TISSUE DISCOMFORT RELIEF

BACKGROUND

Tissue pain, including muscle or pelvic floor pain, is a common problem in men and women alike. Conventional medicine has treated tissue pain in various ways depending on the source of pain. In some patients experiencing pelvic pain, an organ-specific focus is required for treating pelvic pain caused by inflammation in the bladder, prostate gland, or uterus. Also, the pudendal nerve may be entrapped, requiring the release of the nerve. In other instances, an autoimmune process or psychiatric problem may be the cause of discomfort in the pelvic region.

In recent years, it has been found that the majority of pelvic pain is related to muscle dysfunction and muscle related strain. In particular, myofascial pelvic pain (MFPP) can be diagnosed in women by performing vaginal digital palpation of the pelvic floor muscles during routine gynecological exams to examine for the presence of myofascial pelvic pain and trigger points.

Myofascial trigger points are localized painful lumps or nodules in the muscles or associated connective tissue known as fascia, which may be found in various areas of the pelvic floor. In particular, the pelvic floor muscles consist of the superficial muscle layer and the deep muscle layer, which may each contribute to pelvic discomfort. Treatment may be performed in a medical setting or at home. Previously known self-treatment techniques have proven ineffective for an internal or external trigger point release. Existing devices are not well designed for trigger point release and may be dangerous if attempted due to their unsuitable sizes and configurations.

The subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which:

FIG. 10 illustrates another cross-sectional view of the apparatus, and the apparatus is shown as being bent.

DETAILED DESCRIPTION

Figure 1:
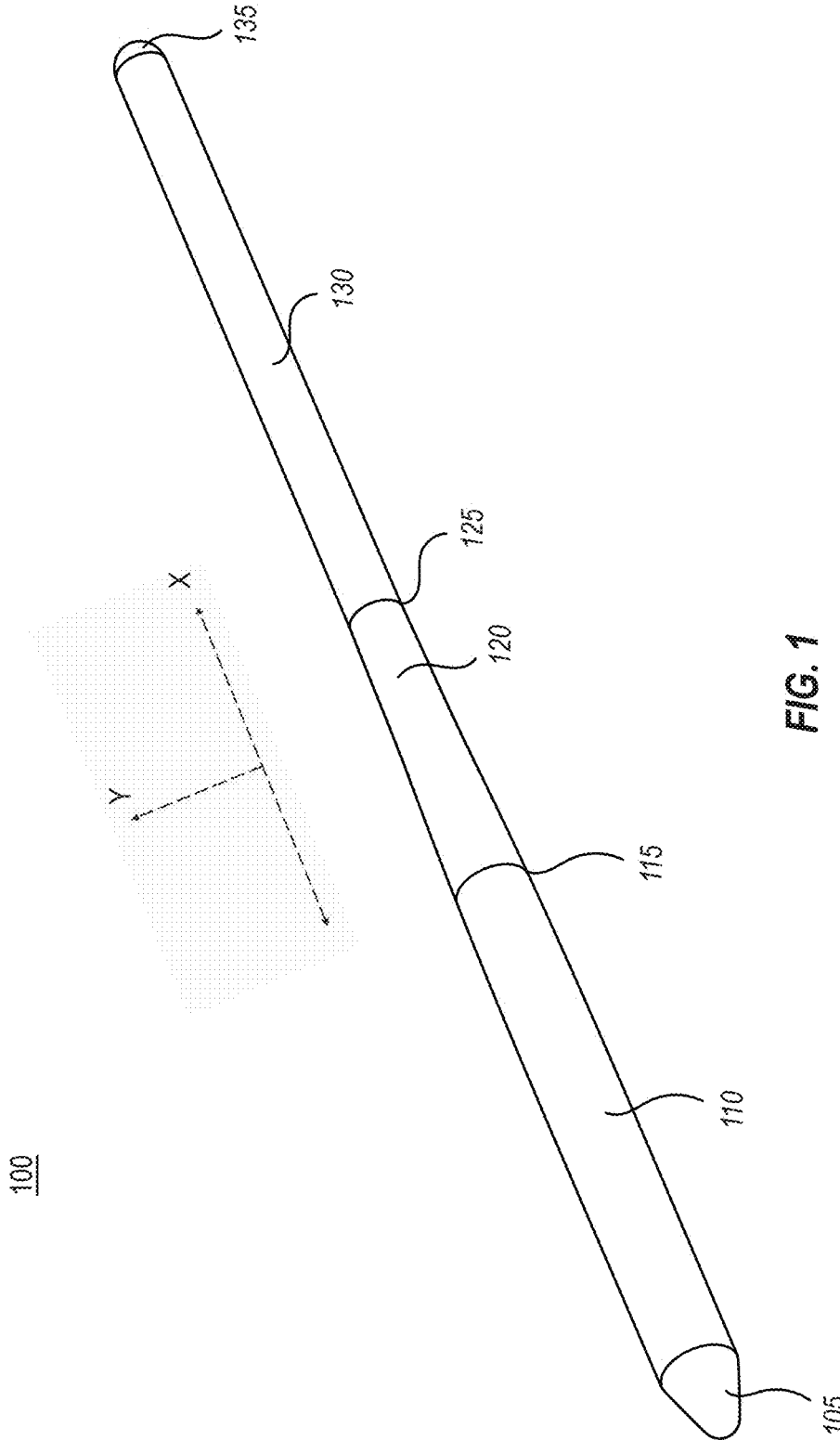
FIG. 1 illustrates an angled perspective view of a therapeutic apparatus.

In general, the embodiments described herein relate to a tissue (e.g., pelvic) trigger point release apparatus suitable for trigger point release and similar therapies related to myofascial or general tissue pain. The apparatus may be inserted into a body cavity or applied externally to relieve pain experienced by the patient. The apparatus may perform strumming, stroking, vibration, heating, cooling, redlight therapy or other wavelengths of infrared (IR) light, and/or other methods of trigger point release on the internal pelvic trigger points and other discomforts associated with pelvic floor pain.

In more detail, the disclosed embodiments are directed to an improved type of apparatus for tissue trigger point therapy. This apparatus includes an elongated core comprising a bendable portion, a first end portion forming a first terminal end of the elongated core, and a second end portion forming a second terminal end of the elongated core. The apparatus further includes an outer covering member that at least partially surrounds the elongated core and that is also bendable with the bendable portion of the elongated core. The bendable portion of the elongated core is bendable in response to an applied bending force that at least meets a threshold amount of force being applied to the bendable portion. The application of the applied bending force to the bendable portion causes the apparatus to be bent into a bent shape, and the apparatus is structured to retain the bent shape after the applied bending force is no longer applied to the bendable portion.

The first end portion is disposed within the apparatus at a first region that is proximate to or overlapping with a first terminal end region of the apparatus, and the second end portion is disposed within the apparatus at a second region that is proximate to or overlapping with a second terminal end region of the apparatus. The first end portion and the second end portions are not bendable, resulting in the first and second regions also not being bendable. This apparatus is usable by a user to help relieve pain.

As used herein, the term "user" relates to a patient, a care provider (e.g., such as a physician, osteopath, nurse, or physical therapist), or another person who uses the apparatus to relieve myofascial pelvic pain. The user may provide care to others or may utilize the apparatus for self-treatment. It should also be noted how the various figures illustrate different features of the disclosed apparatus. Any feature from any of the figures may be combined with any other feature from any of the other figures.

Pelvic floor trigger points may include areas of the muscles of the levator ani, coccygeus, pubococcygeus, puborectalis, obturator internus, piriformis, or other internally accessed trigger points. The apparatus may also beneficially facilitate stretching or stimulation of contracted or shortened internal pelvic floor muscles. The pelvic floor trigger points may be taut bands within the muscle, which can be present at the surface of the muscle, inside the muscle, in the belly of the muscle, or at the attachment(s) of the muscle. Further, the associated connective tissue may be impacted by the apparatus provided in the various embodiments herein.

Having just described some of the various uses of the disclosed apparatus, attention will now be directed to FIG. 1, which illustrates one example implementation of the disclosed apparatus 100. Apparatus 100 is a bendable unit that, when bent in response to an applied external non-gravitational force, can retain its bent shape. A threshold amount of bending force is required to bend the apparatus 100. Often, the threshold amount of force is at least 1 pound of force. For reference, generally, 0.25 pounds of force feels roughly equivalent to feeling the weight of a smaller fruit (e.g., an apple) being held in a person's hand. Thus, 1 pound of force is approximately equivalent to the feeling of about 4 apples in one's hand. The amount of force needed to bend the apparatus 100 is typically a minimum of about 1 pound of force. In some scenarios, the threshold amount of force to bend the apparatus 100 may span from about 0.5 pounds of force to about 5.5 pounds of force. In some scenarios, the range may span from about 1 pound of force to about 5 pounds of force.

It should be noted if the apparatus 100 were initially shaped in the manner shown in FIG. 1 and if a user grasped the apparatus at only one of its terminal ends and then held the apparatus 100 outward in a cantilevered manner, the force of gravity is not sufficient to cause the apparatus 100 to bend. That is, the gravitational force, acting alone on the apparatus 100, is not a sufficient amount of force to cause the apparatus 100 to bend. Thus, as mentioned above, the threshold amount of force that is required to bend apparatus 100 is an external, non-gravitational force.

In some instances, the threshold amount of force may be higher, such as perhaps any value within the range spanning from about 1 pound up to potentially about 5 pounds of force. By having this minimum threshold level of force, the apparatus 100 can be applied to a user's body in a somewhat forceful manner (such as during a massage session), and the apparatus 100 will retain its bent shape despite being pressed against the user's body. Thus, instead of losing its shape when applied to the user's body, the apparatus 100 beneficially retains its shape, provided the applied force does not exceed the threshold level of force.

In FIG. 1, apparatus 100 includes an outer surface material that is typically made of a relatively soft and at least partially flexible material. Regarding term usage, some clarification regarding the difference between "bendable" and "flexible" is warranted.

The term "bendable" (and its variants) generally refers to the ability to be substantially twisted or bent without breaking, and the material can potentially retain a bent shape after an applied force is removed, though in some cases the material may also revert back to its original shape. The term "flexible" (and its variants) generally refers to the ability of a material to undergo a repeated elastic strain, and the material will revert to its original shape after an applied force is removed. Rubber or silicon is generally flexible while a gooseneck table lamp is bendable. As used herein, the term "bendable" does refer to a material that can be bent and that will retain its bent shape after an applied force is removed. As further used herein, the term "bendable" should not be viewed as including a scenario where the material automatically reverts back to its original shape after the bending force is removed.

Returning to FIG. 1, the outer covering member of the apparatus will retain its shape when a force is not exerted against it. When a force is applied to the outer covering member, the outer covering member may somewhat flex. After the force is removed, however, the outer covering member will revert back to its original shape. This flexibility is beneficial because it operates somewhat as a compression buffer when the apparatus is pressed against the user's skin.

Examples of materials that can be used for this outer covering member include, but are not limited to, any type of silicon, rubber, soft plastic, or any other hygienic and flexible material suitable for use potentially inside a user's body. The outer covering member is washable and can be easily cleaned. Typically, the outer covering member does not retain a fragrance or smell after it is washed.

Disposed within the core or internal portion of the apparatus 100 is a bendable gooseneck hose tube member that retains a bent shape after a bending force is exerted against the apparatus 100 and is thereafter removed. For instance, when the apparatus 100 is bent in some manner, the apparatus 100 will retain that bend until a new force is applied to the apparatus 100. A gravitational force, by itself, is not sufficient to cause bending. The bendable nature of the gooseneck hose tube member enables the apparatus 100 to retain a desired shape. As mentioned above, the force required to bend the apparatus 100, including the gooseneck host tube, is the threshold level of force.

Almost any shape can be achieved by bending apparatus 100. Apparatus can be bent into an S-shape, a circular shape, a rounded corner square or rectangular shape, or any other shape. Apparatus 100 can also be bent back into itself, similar to a pretzel-like shape. Apparatus 100 can be repeatedly bent in the same direction, forming a spiral like shape. Apparatus 100 can be repeatedly bent in opposing directions, forming a wave-like shape. Indeed, any shape can be achieved. Symmetrical shapes can be formed, asymmetrical shapes can be formed, and so on, without limit.

The outer covering member can be heat molded onto the gooseneck hose tube member using a heat compression technique. In some cases, during the heat compression, the outer covering member initially is made of two halves, or potentially any number of portions. The gooseneck hose tube member is inserted between the two halves, and then heat compression is applied to adhere the outer covering member to the gooseneck hose tube member and to adhere one half to the other.

The heat compression technique is also performed in a manner so as to avoid having a raised seam existing between the two halves after they are merged together. If, however, a seam is visible, the seam is flush and is not raised relative to the other, non-seam portions of the outer covering member. Thus, the outer covering member is substantially smooth and flush throughout all portions of the apparatus. Ensuring that the seam is not raised is beneficial because it can help avoid scenarios where the seam causes discomfort when contacting the user's body. Optionally, some embodiments may purposefully include ribbing, protrusions, spiraling, or other designs of the outer covering member, where these other designs are structured to facilitate the therapeutic massaging process. Some embodiments can also be formed using a liquid silicone injection mold to form the outer member. Such implementations further limit the seam caused by compression.

As will be described in more detail later, the gooseneck hose tube member is structured to enable the apparatus 100 to retain a desired shape even when a force is being exerted against the apparatus (e.g., when the user is pushing the apparatus 100 against his/her body). Apparatus 100 retains the desired shape provided the amount of applied force is less than the threshold level of force required to bend the apparatus 100. Thus, when the apparatus 100 is being used, a user can bend the apparatus 100 into a specific configuration or shape. The apparatus 100 will then retain that shape, and the user can use the apparatus while the apparatus 100 has the desired shape. As long as an amount of force the user uses when interacting with the apparatus 100 does not exceed the threshold amount of force, then the apparatus 100 will beneficially retain its shape. This is particularly beneficial in situations where the apparatus 100 is being used to reach difficult-to-reach areas, but by bending the apparatus 100 into a specific shape, that area of the user's body can now be easily reached.

As mentioned earlier, often, the threshold amount of force needed to cause the apparatus 100 to bend is a minimum of about 1 pound of force. In some cases, the threshold amount of force may be higher than 1 pound of force, but it is typically less than about 5 pounds of force. The threshold amount of force may be any value within a range of values spanning from about 1 pound of force to about 5 pounds of force.

As will also be described in more detail later, the apparatus 100 includes a thicker portion/diameter and a thinner portion/diameter. Often, the threshold amount of force needed to bend the thicker portion of the apparatus 100 is higher than the threshold amount of force needed to bend the thinner portion of the apparatus 100. For instance, the threshold amount of force to bend the thicker portion (e.g., the first elongated core portion 110) may be a value between about 2 pounds of force to about 5 pounds of force. The threshold amount of force to bend the thinner portion (e.g., the second elongated core portion 130) may be a value between about 1 pound of force to about 3 pounds of force. Of course, different values may be involved, and these are simply examples of some values.

These differences in threshold levels are due to the differences in the thickness of the apparatus 100. The thicker portions require a heighted level of bending force as compared to the thinner portions. Thus, different thresholds of force may be needed to bend the apparatus 100 at different areas of the apparatus 100. As will be described in more detail later, the difference in thickness is typically due to different amounts of the outer covering member being disposed at different positions of the apparatus 100 as opposed to the internal core being different sizes. It should be noted how the primary factor in determining the amount of bending force needed to bend the apparatus 100 is primarily based on the characteristics of the gooseneck hose tube member. The amount of silicone is a secondary factor that has much less of an impact.

Regarding the internal core, the gooseneck hose tube member is also structured in a manner so as to avoid snap-like bending. By "snap-like," it is generally meant that such members are strictly regimented and confined in their bending abilities. For instance, such members may be able to bend only in a specific direction or may be able to bend only a predefined, limited angle as opposed to being about to bend throughout a large range of angles.

In contrast, the gooseneck hose tube member allows for smooth or seemingly continuous bendability of the apparatus 100 throughout at least a majority of the length of the apparatus. The apparatus 100 can be bent in any direction, without limit. Regarding the angle of curvature, the apparatus 100 can also be bent back along itself, evidencing having a tight angle of curvature. Thus, the bending behavior of the apparatus is not discrete, step-like, or snap-like; rather, the bending behavior is fluid-like, smooth, or continuous. The bending behavior is also such that the apparatus can bend throughout a large range of angles. For instance, the apparatus can be bend in a small angle, such as about a 1 degree of bend. The apparatus 100 can also be bend in a coil-like manner, approximating a 360 degrees bend, similar to how a spring appears.

As mentioned, the outer covering member is molded or otherwise coupled to the gooseneck hose tube member. When the apparatus 100 is bent in any manner or direction, one beneficial feature of the outer covering member is that the outer covering member will not "bunch up" or create ribbing. Instead, the outer covering member remains smooth despite being bent, either in a contracted state or a stretched state. This smoothness can help prevent pinching of a user's body when the apparatus 100 is bent and is in contact with the user's body. This beneficial smoothness also prevents the apparatus 100 from catching on or pulling the user's hair. Further details on the gooseneck hose tube member will be provided later with respect to some of the subsequent figures.

In FIG. 1, apparatus 100 is shown as including a first distal or first terminal end region 105. The first terminal end region 105 includes a terminal end or a "tip" located at the end-most portion of the end region 105 (i.e. the left-most portion of the apparatus 100). The tip is structured to be at least partially flexible.

By way of example, when the tip is used to contact a user's body, the tip's shape can partially deform and flex in various manners and directions. Thus, instead of a hard or rigid tip, apparatus 100 has a softer, some-what malleable tip that is structured to be flexible. When the tip contacts a user's body, the flexibility of the tip helps provide comfort to the user's body due to its flexible characteristics.

The first terminal end region 105 is also shown as generally having a tapered portion that extends from the tip to a first elongated core portion 110 of the apparatus 100. One will appreciate how the length of the tapered portion can be modified to accommodate different design constraints. The tapered portion approximates that of a cone.

Optionally, the first terminal end region 105 can be structured to support other types of end regions, such as bulbous ends, semi-spherical ends, or any other shaped end. Optionally, some embodiments are structured to enable swapping of tip types. For instance, the first terminal end region 105 may be affixed to the apparatus 100 using a screw member or perhaps even a magnetic member. Different tips can be used by replacing one tip with another. As one example, the conical tip shown in FIG. 1 can, in some embodiments, be removed and replaced with a bulbous tip.

Regarding the first elongated core portion 110, the first elongated core portion 110 extends from the first terminal end region 105 to a first transition portion 115 of apparatus 100. Notice, the diameter of the first elongated core portion 110 is generally uniform throughout the entire length of the first elongated core portion 110. Often, the diameter of the first elongated core portion 110 is a value within a range spanning from about 0.4 inches (e.g., about 1 centimeter) to about 1.6 inches (e.g., about 4 centimeters). In some embodiments, the diameter can be larger than 0.4 inches (e.g., about 1 centimeter), such as perhaps up to about 2 inches (e.g., about 5 centimeters) or even up to about 2.4 inches (e.g., about 6 centimeters). Typically, the diameter of the first elongated core portion 110 is approximately 0.8 inches (e.g., about 2 centimeters).

In some embodiments, the diameter of the first elongated core portion 110 may not be uniform. For instance, the apparatus 100 may include ribbing, spiraling, or other protrusion features along the length of the first elongated core portion 110. If the first elongated core portion 110 includes these features, then the diameter of the first elongated core portion 110 may not be uniform. Despite not being uniform in diameter, it is typically the case that the diameter of the first elongated core portion 110 is a minimum of 0.4 inches (e.g., about 1 centimeter).

Starting at the first transition portion 115, the diameter of the apparatus 100 progressively changes from the diameter of the first elongated core portion 110 to a relatively smaller diameter. This progressive change in diameter occurs from the first transition portion 115 to the second transition portion 125. For instance, the changing diameter of the transition portion may be a value within a range spanning from about a maximum of 1.6 inches (e.g., about 4 centimeters or whatever value corresponds to the diameter of the first elongated core portion 110) to about a minimum of 0.4 inches (e.g., about 1 centimeter or whatever value corresponds to the diameter of the second elongated core portion 130). In some scenarios, the maximum and minimum diameters of the apparatus, including the diameter(s) of the transition portion, can be any value within a range spanning from about 2.5 inches to about 0.25 inches.

As one example, assume the thicker diameter is 1 inch (e.g., about 2.5 centimeters) and the thinner diameter is 0.6 inches (e.g., about 1.5 centimeters). Further, assume the length of the transition region is 1 inch (e.g., about 2.5 centimeters). The transition region progressively transitions from the 1 inch diameter to the 0.6 inch diameter throughout the 1 inch length of the transition region. Typically, the progressive transition is linear. In some instances, however, the transition may be non-linear in its progression.

FIG. 1 shows the transition region (i.e. the region between the first transition portion 115 and the second transition portion 125) as being approximately in the center of the apparatus, as shown by the center part 120 being included within the transition region. Such a configuration is not a requirement, however. In some scenarios, the transition region may fall on either side of the center part 120 and may not include the center part 120. In some scenarios, the center part 120 may be included in the transition region, but the center part 120 of the apparatus 100 may not be the center of the transition region. For instance, the center part 120 of the apparatus 100 may be to the left or to the right of the center of the transition region.

The length of the apparatus 100 is often from about 8 inches (e.g., about 0.2 meters) to about 20 inches (e.g., about 0.5 meters). In some scenarios, the length can be longer than about 20 inches, such as any value from about 8 inches to about 36 inches. The length of the first elongated core portion 110 is typically a value within the range spanning from about 3 inches to about 12 inches. The length of the transition region (i.e. the region spanning from the first transition portion 115 to the second transition portion 125) is typically a value within the range spanning from about 1 inch to about 6 inches. As will be described shortly, the length of the second elongated core portion 130 is typically a value within the range spanning from about 3 inches to about 12 inches. In some scenarios, the length of the second elongated core portion 130 is the same as the length of the first elongated core portion 110. In other scenarios, the lengths of those two portions are different.

Starting at the second transition portion 125 and extending to the opposite end of the apparatus 100 (opposite relative to the first terminal end region 105), the diameter of the apparatus 100 is again generally uniform throughout the length of a second elongated core portion 130. The diameter of the second elongated core portion 130 is a value within a range spanning from about 0.2 inches (e.g., about 0.5 centimeters) to about 0.6 inches (e.g., about 1.5 centimeters). In some embodiments, the diameter can be larger, though the diameter of the second elongated core portion 130 is always smaller than the diameter of the first elongated core portion 110.

Typically, the diameter of the second elongated core portion 130 is less than or equal to about 70% the diameter of the first elongated core portion 110. In some cases, the diameter of the second elongated core portion 130 is a percentage value relative to the diameter of the first elongated core portion 110, such as a value within the following range of percentage values: any value from about 10% up to about 90%. Often, the range is from about 30% to about 60%.

Thus, the transition portion of the apparatus 100, which extends from the first transition portion 115 to the second transition portion 125 enables the apparatus 100 to progressively transition from the diameter of the first elongated core portion 110 to the diameter of the second elongated core portion 130. Assuming the diameter of the first elongated core portion 110 corresponds to a maximum thickness or diameter of the apparatus 100, that diameter can be viewed as having a 100% thickness. Further, assuming the diameter of the second elongated core portion 110 is less than or equal to a variable percentage value of the diameter of the first elongated core portion 110, the transition region causes the diameter of the apparatus to transition from having a 100% thickness to having less than or equal to the variable percentage value in terms of thickness.

Apparatus 100 includes a second terminal end region 135 that is disposed at an opposite end of the apparatus 100 relative to the first terminal end region 105. In some implementations, the second terminal end region 135 includes a bulbous knob at the end, where the largest diameter of the bulbous knob is larger than the diameter of the second elongated core portion 130 but still smaller than the diameter of the first elongated core portion 110. Optionally, the largest diameter of the bulbous knob may be any percentage value relative to the largest diameter of the second elongated core portion 130, where example values range from about 101% to about 150%, while still ensuring that the largest diameter of the bulbous knob is smaller than the diameter of the first elongated core portion 110. In some embodiments, the largest diameter of the bulbous knob is larger than the diameter of the first elongated core portion 110.

In some implementations, the second terminal end region 135 includes a spherical knob whose largest diameter is the same as the diameter of the second elongated core portion 130. In some implementations, the second terminal end region 135 has a non-spherical shape, such as perhaps a conical shape. Other shapes are also conceived. Similar to the first terminal end region 105, some embodiments permit the second terminal end region 135 to be swappable with different end types.

Notice also, FIG. 1 shows an X-Y legend positioned approximately in the center of the apparatus 100. Apparatus 100 is symmetrical along a parallel, central axis (i.e. the X axis), which extends along a length-wise direction of the apparatus. Apparatus 100 is asymmetrical along a perpendicular, central axis (e.g., the Y-axis), which is positioned at a length-wise center point of the apparatus.

Figures 2, 3, 4, 5, 6, 7:
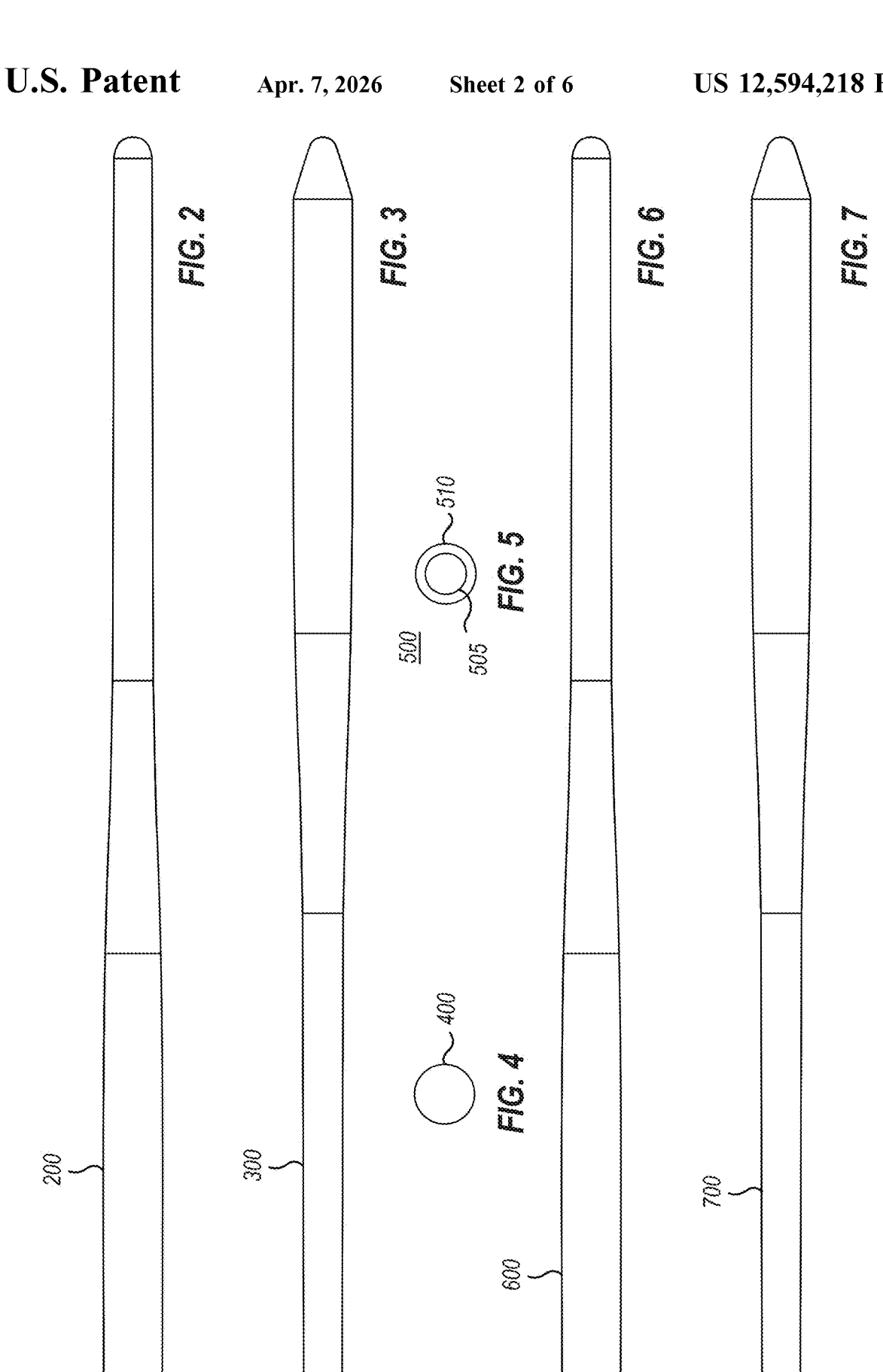
FIG. 2 illustrates a left-hand side perspective view of the apparatus.
FIG. 3 illustrates right-hand side perspective view of the apparatus.
FIG. 4 illustrates a front perspective view of the apparatus.
FIG. 5 illustrates a rear perspective view of the apparatus.
FIG. 6 illustrates a top aerial view looking down at the apparatus.
FIG. 7 illustrates bottom view looking up at the apparatus.

FIG. 2 shows a left-hand view 200 of the apparatus 100. FIG. 3 shows a right-hand view 300 of the apparatus 100. FIG. 4 shows a front perspective view 400 of the apparatus 100 looking at the apparatus 100 from the first terminal end region 105 point of view. FIG. 5, on the other hand, shows a rear perspective view 500 of the apparatus 100 looking at the apparatus 100 from the second terminal end region 135.

Notice, in FIG. 5, the reference label 505 is directed to an inner concentric ring. This inner concentric ring corresponds to the smaller diameter of the second elongated core portion 130. The reference label 510 is directed to an outer concentric ring. This outer concentric ring corresponds to the larger diameter of the first elongated core portion 110.

FIG. 6 shows a top aerial view 600 looking down at the apparatus 100. FIG. 7 shows a bottom view 700 looking up at the apparatus 100. Thus, FIGS. 2, 3, 4, 5, 6, and 7 show a left view, a right view, a front view, a rear view, a top view, and a bottom view of the apparatus 100.

Figure 8:
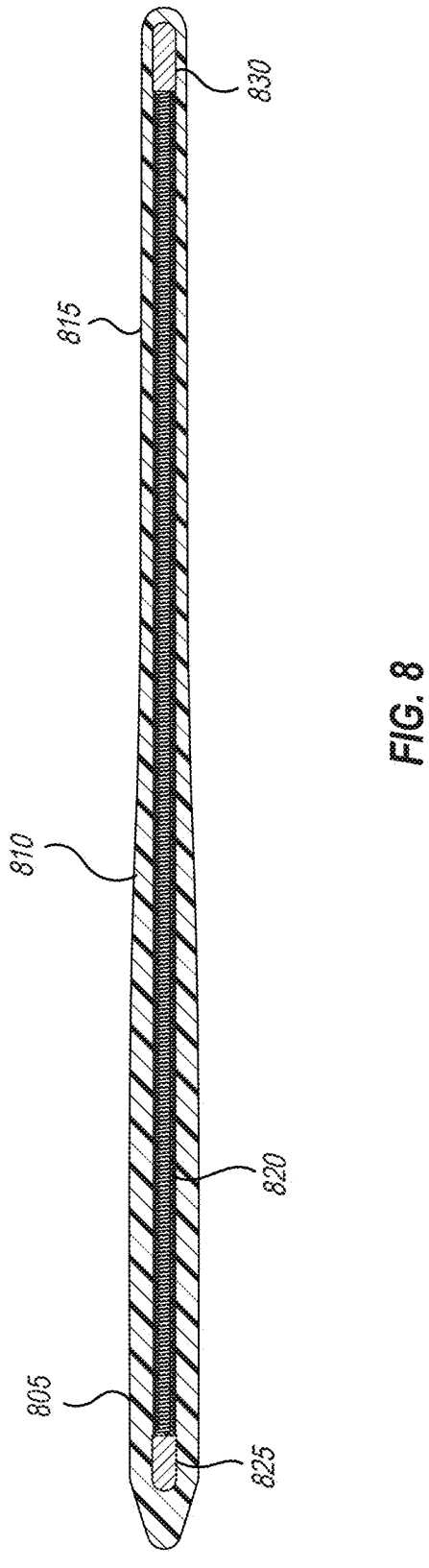
FIG. 8 illustrates a cross-sectional view of the apparatus.

FIG. 8 shows one example implementation of the apparatus 800, which corresponds to the apparatus 100 of FIG. 1. In particular, FIG. 8 shows a cross-sectional cut away view of the apparatus 800.

As mentioned previously, the apparatus 800 includes an outer covering member or outer membrane and an inner core made of the gooseneck hose tube member. The outer covering member is illustrated in FIG. 8 via the right-ward directed diagonal lines. The outer covering member can be made of any semi-flexible material, one example of which is silicon, as described previously.

Apparatus 800 also includes an inner core, as reflected by the combination of the left-ward directed diagonal lines and the vertical lines running the length of apparatus 100. This combination of lines represent the gooseneck hose tube member mentioned earlier.

In more detail, apparatus 800 includes a first elongated core portion 805, which corresponds to the first elongated core portion 110 of FIG. 1. Apparatus 800 also includes a transition region 810, which corresponds to the length of the apparatus 100 spanning the distance between the first transition portion 115 and the second transition portion 125 in FIG. 1. Apparatus 800 also includes a second elongated core portion 815, which corresponds to the second elongated core portion 130 of FIG. 1.

FIG. 8 also illustrates the core of the apparatus 800. This core includes a gooseneck hose tube member 820, a first end portion 825, and a second end portion 830. Thus, reference to the "core" of the apparatus 800 refers to the combination of the bendable gooseneck hose tube member 820 and the first and second end portions 825 and 830. The end portions 825 and 830 may comprise an extended portion of the gooseneck hose tube member 820 or any type of cap-like end unit. The cap-like end unit may be comprised of any type of material, such as plastic, silicone, metal, and so on, without limit. The length of the first and second end portions 825 and 830 can vary as well, as will be described in more detail shortly. In some scenarios, the cap-like end may quite minimal and is used to ensure the spring and coil portions of the gooseneck hose tube member do not unravel.

As shown, the core extends throughout at least a majority of the length of the apparatus 800. Often, the core extends throughout at least 90% of the length of the apparatus 800. In some instances, the core extends throughout at least 95% of the length of the apparatus 800.

It should be noted that the first end portion 825 and the second end portion 830 are structured to be rigid and non-bendable. The gooseneck hose tube member 820, on the other hand, is structured to be bendable in the manner described previously. Typically, the relative length of the first end portion 825 is less than about 10% of the entire length of the core. Similarly, the relative length of the second end portion 830 is less than about 10% of the entire length of the core. The length of the gooseneck hose tube member 820 is typically at least and is often more than about 80% of the entire length of the core. Often, the length of the gooseneck hose tube member 820 is more than about 90% of the length of the core.

In some scenarios, the lengths of the first and second end portions 825 and 830 are the same. In other scenarios, the lengths of the first and second end portions 825 and 830 are different. These lengths may be any value within a range spanning from about 0.25 inches to about 2 inches.

Because the first and second end portions 825 and 830 are rigid and are not bendable, the portions of the apparatus 800 where those first and second end portions 825 and 830 are disposed are generally not bendable. The portions of the apparatus 800 where the gooseneck hose tube member 820 is disposed is bendable, however.

The core is embedded in or enveloped by the outer covering member. Notice, the first end portion 825 terminates (along the length of the apparatus) some distance (i.e. a "first separation distance") away from the left-most terminal end of the apparatus 800. In some instances, the distance separating the outermost part of the first end portion 825 and the left-most terminal end of the apparatus 800 is a value within a range spanning from about 0.25 inches to about 1 inch.

Similarly, the second end portion 830 terminates (along the length of the apparatus) some distance (i.e. a "second separation distance") away from the right-most terminal end of the apparatus 800. In some instances, the distance separating the outermost part of the second end portion 830 and the right-most terminal end of the apparatus 800 is a value within a range spanning from about 0.1 inches to about 0.6 inches. Typically, the first separation distance is larger than the second separation distance. In some scenarios, however, the first and second separation distances may be the same.

In some cases, the second separation distance is between about $\frac{1}{10}$ to about $\frac{1}{2}$ that of the first separation distance. That is, the second separation distance may be from about $\frac{1}{10}$ to about $\frac{1}{2}$ that of the first separation distance.

Because the second end portion 830 is relatively closer to its corresponding terminal end of the apparatus 800 (i.e. the "second" terminal end) as compared to the first end portion 825 relative to its corresponding terminal end of the apparatus (i.e. the "first" terminal end), a relatively smaller amount of the outer covering member is disposed at the second terminal end as compared to the first terminal end.

In some embodiments, because a relatively smaller amount of the outer covering member is disposed at the second terminal end, the second terminal end is relatively less flexible, malleable, adjustable, or bendable relative to the first terminal end due to there being a smaller amount of the outer covering member at that location. Thus, from a user's perspective, the second terminal end may be used as a more rigid surface and can be used to aggressively massage painful areas. The first terminal end, on the other hand, provides a relatively less rigid surface and can be used to more carefully or more softly massage painful areas.

FIG. 8 shows how the apparatus 800 progressively transitions from a thicker diameter to a thinner diameter. Notice, the diameter of the core remains substantially the same throughout the length of the apparatus 800. The change in diameter of the apparatus 800 is typically achieved due to changes in the thickness of the outer covering member as opposed to changes in thickness of the core.

For instance, along the length of the thicker portion of the apparatus 800, the outer covering member is shown as being relatively thicker as compared to the thickness of the outer covering member along the length of the thinner portion of the apparatus 800. In the transition region, the thickness of the outer covering member progressively changes. Thus, in FIG. 8, the change in diameter of the apparatus 800 is not due to changes in the diameter of the core but rather is due to changes in the thickness of the outer covering member. In other scenarios, however, the thickness of the core may not be uniform and can contribute to the differences in the thickness of the apparatus 800.

Regarding the characteristics of the core, the core includes the gooseneck hose tube member 820, the first end portion 825, and the second end portion 830. The gooseneck hose tube member 820 includes an inner spring portion and an outer wire portion that is at least partially compressed into the coils of the spring. The compression of the outer wire portion into the coils of the spring provide increased stiffness and enables the gooseneck hose tube member 820 to retain its shape when bent. If the gooseneck hose tube member 820 included only the spring portion, then the gooseneck hose tube member 820 would spring back or revert back to its original shape after a bending force was removed. By including the outer wire portion wrapped around the spring coils, the combination of the spring portion and the outer wire portion enable the gooseneck hose tube member 820 to be bent and to retain its bent shape even after the bending force is removed.

The gooseneck hose tube member 820 is typically made of steel. Other materials can be used as well, such as different metal types or potentially even plastic. The first and second end portions 825 and 830 are typically made of the same material as the gooseneck hose tube member 820. In some scenarios, however, the first and second end portions 825 and 830 are made of a different material relative to the material forming the gooseneck hose tube member 820.

The length of the first and second end portions 825 and 830 may be the same or they may be different. Often, the lengths of these portions is a value within a range spanning from about 0.25 inches to about 2.0 inches.

Because the first and second end portions 825 and 830 are rigid, the lengths of the apparatus 800 where the first end portion 825 is disposed and where the second end portion 830 are disposed are generally not bendable. That is, each of those non-bendable lengths of the apparatus 800 is typically some length from about 0.25 inches to about 2.0 inches.

Figure 9:
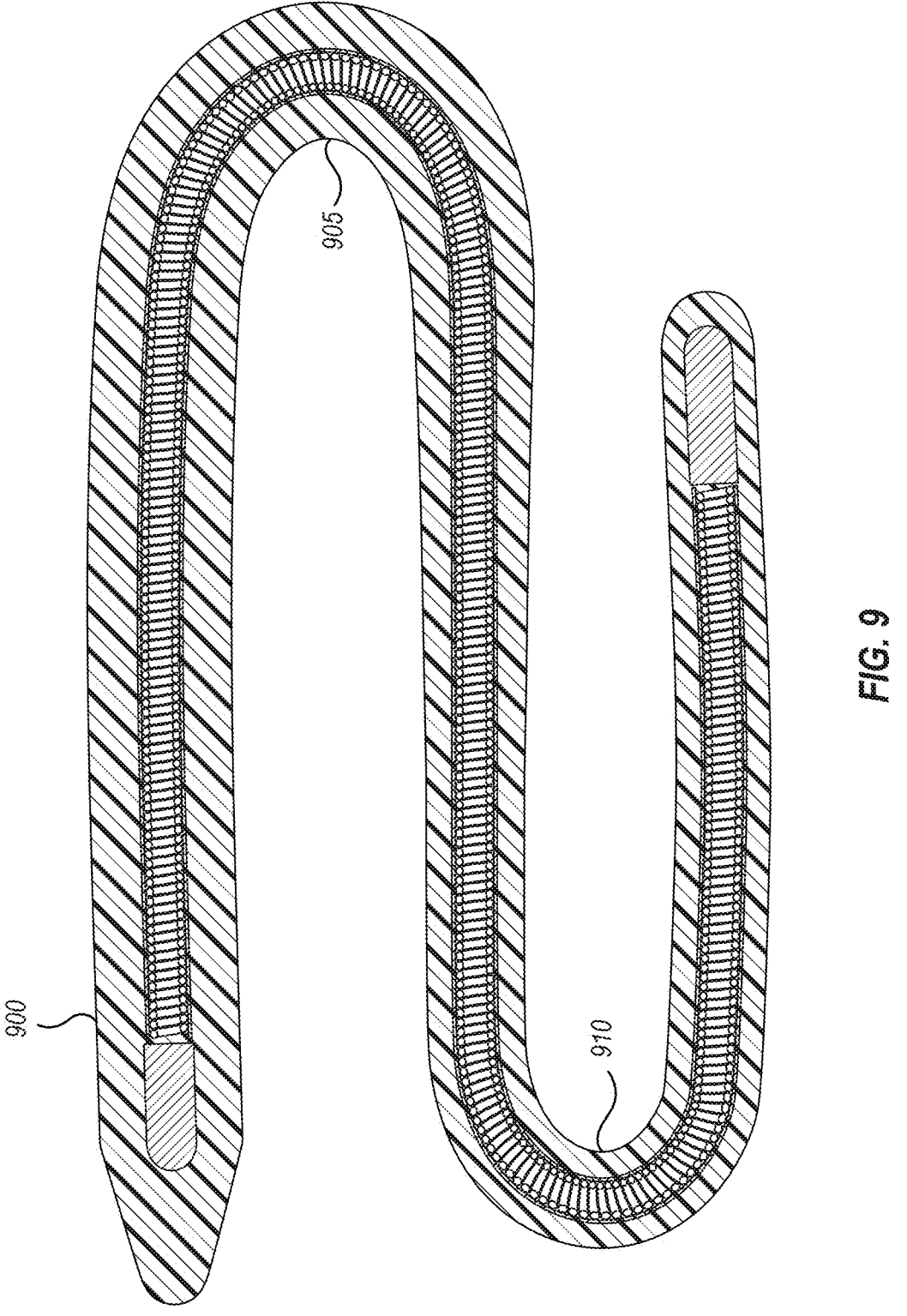
FIG. 9 illustrates a cross-sectional view of the apparatus, and the apparatus is shown as being bent.

FIG. 9 shows another cross-sectional view of apparatus 900, which corresponds to the apparatuses mentioned thus far. In FIG. 9, apparatus 900 is shown as having a first bend 905 and a second bend 910. These bends persist even after the bending force is removed from the apparatus 900.

In FIG. 9, the first bend 905 can be considered as a "concave" bend. The second bend 910 can be considered as being a "convex" bend. These different bend angles and types illustrate how the apparatus 900 is bendable in any direction. FIG. 9 shows how the apparatus 900 is generally bend in a backwards S-shape.

The first bend 905 is made along the thicker portion of apparatus 900. The second bend 910 is made along the thinner portion of apparatus 900. Notice, the radius of curvature of the first bend 905 is larger than the radius of curvature of the second bend 910. The difference in the radii of curvatures is due to the difference in the diameters of the different regions or portions that are being bent. If the apparatus 900 is bent at its thicker regions, then the bend will have a relatively larger radius of curvature. If the apparatus 900 is bent at its thinner regions, then the bend will have a relative smaller radius of curvature. If the apparatus were bent in the central transition region, then a different radius of curvature will be apparent because of the difference in diameter at that region.

Although FIG. 9 emphasizes only two bends or regions that are bent, one will appreciate how a substantial majority of the length of the apparatus 900 can be bent. Notice also, the outer covering member is not rippling or bunching up on the inner curves of the bends, such as at the location where the reference line for the first bend 905 is directed or at the location where the reference line for the second bend 910 is directed. FIG. 9 also provides another viewpoint of the gooseneck hose tube member, including the spring portion and the outer wire portion.

FIG. 10 illustrates an apparatus 1000, which corresponds to the apparatuses mentioned thus far. FIG. 10 demonstrates how the terminal end regions of apparatus 1000 are not bendable due to the position and placement of the first and second end portions, which restrict bendability at their respective positions. FIG. 10 shows a first bend 1005, a first region 1010, a second bend 1015, and a second region 1020.

The first region 1010 includes the terminal end region mentioned earlier as well as an end portion. Because the first region 1010 includes the end portion, the first region 1010 is not bendable to accommodate a bend like the first bend 1005. That is, while the apparatus 1000 is freely bendable up to the first region 1010, the bendability of the apparatus 1000 becomes restricted at the first region 1010 because of the end portion. The end portion is rigid and prevents the apparatus 1000 from bending at that location.

Similarly, the second region 1020 includes a terminal end region as well as an end portion. Because the second region 1020 includes the end portion, the second region 1020 is not bendable to accommodate a bend like the second bend 1015. That is, while the apparatus 1000 is freely bendable up to the second region 1020, the bendability of the apparatus 1000 becomes restricted at the second region 1020 because of the end portion. The end portion is rigid and prevents the apparatus 1000 from bending at that location.

Figure 11:
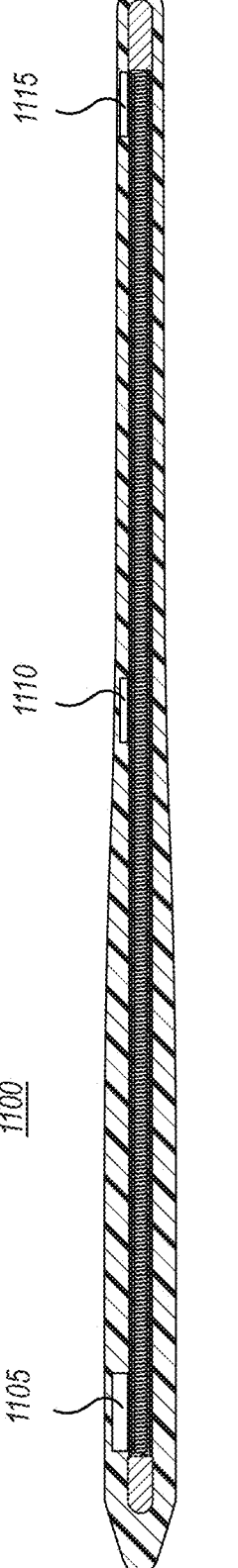
FIG. 11 illustrates different battery-powered elements that can be disposed within the apparatus.

FIG. 11 shows another cross-sectional view of an apparatus 1100, which corresponds to the apparatuses mentioned thus far. In some implementations, the apparatus includes one or more of a heating element 1105, a vibration element 1110, a cooling element 1115, or other elements, such as perhaps a red light element. The position of these elements is not required to be at the positions indicated in FIG. 11. Instead, the heating element 1105, the vibration element 1110, and/or the cooling element 1115 (or any other element) can be disposed at any position along the length of the apparatus, without limit. In some scenarios, the elements are positioned so as to abut one another. In other scenarios, a gap or separation distance exists between the elements, as is currently shown in FIG. 11.

In some scenarios, the elements are disposed along the same length portion as where the end portions are disposed. For instance, the element 1105 may be disposed on top of (relative to the perspective shown in FIG. 11) the end portion. In such scenarios, because the end portions already restrict the bendability of the apparatus, the elements (which are disposed along the same length of the apparatus where the end portions are disposed) would not further contribute to restricting the bendability of the apparatus. In some scenarios, the elements are disposed in the middle portion of the apparatus, and the vibrations, heat, or cooling provided by those elements permeate throughout the length of the apparatus. These elements may contact the gooseneck hose tube member and may be at least partially embedded within the outer covering member.

Optionally, these elements are battery powered. The battery can be charged in different ways. One example charging technique is induction charging. Another example charging technique is a wired charging, with a charging wire portion being insertable into the outer covering member of the apparatus to reach the inner elements. Another example charging technique includes providing exposed charging terminals or exposed nubs on the apparatus 1100, where these exposed nubs are flush with the outer surface of the outer covering member. In some implementations, the exposed nubs might not be flush with the outer covering member and might be either indented within the outer covering member or protruding partially out of the outer covering member.

A charging device (e.g., perhaps having a magnet to enable streamlined coupling) can be coupled to these nubs to charge the underlying battery. When exposed nubs are used as the charging mechanism, it is typically the case that these exposed nubs are disposed at or near the central portion of the apparatus to avoid having those exposed nubs being insertable into a user's body cavity. Thus, these different elements can be charged in any suitable manner.

It should be noted how, in at least some embodiments, the portion of the apparatus where one or more of these elements is disposed may be restricted in terms of its bendability. In some cases, the portion may still be somewhat bendable, but it is relatively less bendable as compared to a portion of the apparatus where no element is disposed. In some cases, the portion having the element(s) is rigid, similar to rigidity of the end portions mentioned above. Thus, in some embodiments, the placement of these elements can result in specific portions or regions of the apparatus being less bendable or perhaps not bendable.

In some scenarios, the apparatus may include a red light therapy device. This type of device can shine or direct therapeutic red light onto a portion of a user's body. Optionally, the red light device can be embedded within the apparatus, and the apparatus may include a transparent window that avoids filtering the red light and that allows the red light to emanate outward from within the apparatus. Other types of lighting elements can be used as well, without limit.

Optionally, a node or waveguide can extend from the lighting element (e.g., the red light therapy device) through the outer covering member. The node can allow the light to emanate from the internal portion of the apparatus to the outside of the apparatus. Optionally, the node can be flush with the outer surface of the outer covering member. In some cases, the node can protrude slightly from the outer surface of the outer covering member.

In some embodiments, the core may be comprised of a single gooseneck hose tube member having uniform diameter, as shown in FIG. 11. In alternative embodiments, the core may be comprised of multiple different gooseneck hose tube members, each having a different diameter. For instance, the core may include a first gooseneck hose tube member disposed in a first portion of the apparatus and a second gooseneck hose tube member disposed in a second portion of the apparatus. The characteristics (e.g., length, diameter, required threshold amount of force to bend) of the first gooseneck hose tube member may be different than the characteristics of the second gooseneck hose tube member. In some embodiments, the diameter of the apparatus may differ depending on the placement of another component, such as a vibration component, battery component, redlight component, or heating or cooling component. For instance, the placement of a given component may cause the local diameter of the apparatus at that placement to be larger than the diameters of the surrounding portions of the apparatus.

Thus, the placement of a component can result in a larger diameter of the apparatus at that placement location.

The two members may meet at the transition portion of the apparatus. Optionally, at the location where the two member meet, the flexibility of the apparatus may be limited or restricted entirely at that specific location. In some scenarios, the two members may meet at a location that is different than at the transition portion. In some scenarios, more than two gooseneck hose tube members may be involved and included.

Referring back to FIG. 8, FIG. 8 shows an apparatus 800 for tissue trigger point therapy. Apparatus 800 includes an elongated core comprising a bendable portion (e.g., the gooseneck hose tube member 820), a first end portion (e.g., the first end portion 825) forming a first terminal end of the elongated core, and a second end portion (e.g., second end portion 830) forming a second terminal end of the elongated core.

Apparatus 800 also includes an outer covering member (e.g., the portion referenced using the rightward diagonal lines). This outer covering member entirely or at least partially surrounds the elongated core. This outer covering member is also bendable with the bendable portion of the elongated core.

The outer covering member is made of silicon, plastic, or rubber. The outer covering member may be formed from at least two silicon members that are coupled together. Beneficially, a seam between the at least two silicon members is flush and is not raised relative to the non-seam portions of the outer covering member.

The bendable portion of the elongated core is bendable in response to an applied bending force that at least meets a threshold amount of force being applied to the bendable portion. The threshold amount of force needed to bend the bendable portion is at least 1 pound of force. In some scenarios, the threshold amount of force needed to bend the bendable portion is a value within a range spanning from about 1 pound of force to about 5 pounds of force, though different ranges are conceived.

Application of the applied bending force to the bendable portion causes the apparatus to be bent into a bent shape. Almost any shape can be formed, including shapes that bend into themselves, such as a pretzel-like shape.

The apparatus is structured to retain the bent shape after the applied bending force is no longer applied to the bendable portion. Thus, the exclusive application of gravity is not sufficient to cause the apparatus to lose its shape or to take on a new shape. Only the application of an external, non-gravitational force is sufficient to cause the apparatus to have its shape modified. This external, non-gravitational force is typically provided from the user's own strength and hands.

The first end portion is disposed within the apparatus at a first region that is proximate to (or even at least partially overlapping with) a first terminal end region of the apparatus. For instance, the first end portion 825 of FIG. 8 is disposed near (or overlaps with) the first terminal end region 105 of FIG. 1. Similarly the second end portion is disposed within the apparatus at a second region that is proximate to (or even at least partially overlapping with) a second terminal end region of the apparatus. For instance, the second end portion 830 of FIG. 8 is disposed near (or overlaps with) the second terminal end region 135 of FIG. 1.

The first end portion and the second end portions are not bendable, resulting in the first and second regions also not being bendable. FIG. 10 shows how the first and second regions are not bendable. In some embodiments, a length of the first end portion, which is not bendable and which causes the first region to also not be bendable, is at least 0.5 inches in length. In some embodiments, a length of the second end portion, which is not bendable and which causes the second region to also not be bendable, is at least 0.5 inches in length.

In some embodiments, the bendable portion of the elongated core is made of a gooseneck hose tube member. This gooseneck hose tube member includes a spring portion and an outer wire portion compressed between coils of the spring portion.

Optionally, the apparatus is divisible into three different segments based on differences in diameter; the three different segments including a first segment, a second segment, and a third segment. The first segment (e.g., the first elongated core portion 110 of FIG. 1) has a first maximum thickness. The third segment (e.g., the second elongated core portion 130 of FIG. 1) has a second maximum thickness that is smaller than the first maximum thickness. The second segment (e.g., the transition region spanning the length between the first transition portion 115 of FIG. 1 and the second transition portion 125) is a transition segment that progressively transitions from having the first maximum thickness to having the second maximum thickness.

When bent to a maximum amount, a radius of curvature of the first segment is a first radius of curvature, as shown by the first bend 905 of FIG. 9. When bent to a maximum amount, a radius of curvature of the third segment is a second radius of curvature, as shown by the second bend 910 of FIG. 9. The first radius of curvature is larger than the second radius of curvature.

Optionally, a length of the second segment is at least 1 inch in length. Optionally, a length of the first segment is at least 4 inches. As another option, a length of the third segment is at least 4 inches. In some scenarios, a length of the apparatus is at least 12 inches.

In some implementations, the first terminal end region of the apparatus includes a cone-like end tip, as shown in FIG. 1 by the cone-like tip in the first terminal end region 105. This cone-like end tip is at least partially flexible and compressible when pressed against an external body.

In some implementations, the second terminal end region of the apparatus includes a semi-spherical end tip, as shown in FIG. 1 by the semi-spherical end tip in the second terminal end region 135. This semi-spherical end tip is substantially not compressible when pressed against an external body.

As shown in FIG. 1, apparatus 100 is symmetrical along a parallel, central axis (e.g., the X-Axis) extending along a length-wise direction of the apparatus. Apparatus 100 is asymmetrical along a perpendicular, central axis (e.g., the Y-axis) positioned at a length-wise center point of the apparatus.

The present invention may be embodied in other specific forms without departing from its characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for tissue trigger point therapy, said apparatus comprising:

an elongated core comprising a bendable portion, a first end portion forming a first terminal end of the elongated core, and a second end portion forming a second terminal end of the elongated core; and an outer covering member that at least partially surrounds the elongated core and that is also bendable with the bendable portion of the elongated core, wherein:

the bendable portion of the elongated core is bendable in response to an applied bending force that at least meets a threshold amount of force being applied to the bendable portion, the bendable portion is comprised of a first gooseneck hose tube member and a second gooseneck hose tube member, the first gooseneck hose tube member having a first bending force threshold and the second gooseneck hose tube member having a second bending force threshold, such that different portions of the bendable portion have different bending force thresholds, application of the applied bending force to the bendable portion causes the apparatus to be bent into a bent shape, the apparatus is structured to retain the bent shape after the applied bending force is no longer applied to the bendable portion, the first end portion is disposed within the apparatus at a first region that is proximate to or overlapping with a first terminal end region of the apparatus, and the second end portion is disposed within the apparatus at a second region that is proximate to or overlapping with a second terminal end region of the apparatus, the first end portion and the second end portions are not bendable, resulting in the first and second regions also not being bendable, when the apparatus is straightened into an unbent shape, a combination of the bendable portion and the outer covering member is asymmetrical along a perpendicular, central axis positioned at a length-wise center point of the apparatus, said combination being asymmetrical as a result of a progressive thickening of a portion of the outer covering member, and when the apparatus is straightened into the unbent shape, said combination has rotational symmetry along a central axis that extends along a length-wise direction of the apparatus.

2. The apparatus of claim 1, wherein the threshold amount of force needed to bend the bendable portion is at least 1 pound of force.

3. The apparatus of claim 1, wherein the outer covering member is made of silicone, plastic, or rubber.

4. The apparatus of claim 1, wherein the bendable portion of the elongated core is made of a gooseneck hose tube member comprising a spring portion and an outer wire portion compressed between coils of the spring portion.

5. The apparatus of claim 1, wherein a length of the first end portion, which is not bendable and which causes the first region to also not be bendable, is at least 0.5 inches in length.

6. The apparatus of claim 1, wherein a length of the second end portion, which is not bendable and which causes the second region to also not be bendable, is at least 0.5 inches in length.

7. The apparatus of claim 1, wherein the outer covering member is formed from at least two silicon members that are coupled together, and wherein a seam between the at least two silicon members is flush and is not raised relative to non-seam portions of the apparatus.

8. The apparatus of claim 1, wherein:

the apparatus is divisible into three different segments based on differences in diameter, the three different segments including a first segment, a second segment, and a third segment, the first segment has a first maximum thickness, the third segment has a second maximum thickness that is smaller than the first maximum thickness, and the second segment is a transition segment that progressively transitions from having the first maximum thickness to having the second maximum thickness.

9. The apparatus of claim 8, wherein a length of the second segment is at least 1 inch in length.

10. The apparatus of claim 9, wherein a length of the first segment is at least 4 inches.

11. The apparatus of claim 10, wherein a length of the third segment is at least 4 inches.

12. The apparatus of claim 1, wherein a length of the apparatus is at least 12 inches.

13. The apparatus of claim 1, wherein the first terminal end region of the apparatus includes a cone-like end tip that is at least partially flexible and compressible when pressed against an external body.

14. The apparatus of claim 1, wherein the second terminal end region of the apparatus includes a semi-spherical end tip that is substantially not compressible when pressed against an external body.

15. The apparatus of claim 1, wherein the apparatus is asymmetrical when bisected in half at a center point along a length of the apparatus.

16. The apparatus of claim 1, wherein the threshold amount of force needed to bend the bendable portion is a value within a range spanning from 1 pound of force to 5 pounds of force.

17. The apparatus of claim 1, wherein:

the apparatus is divisible into three different segments based on differences in diameter, the three different segments including a first segment, a second segment, and a third segment, the first segment has a first maximum thickness, the third segment has a second maximum thickness that is smaller than the first maximum thickness, the second segment is a transition segment that progressively transitions from having the first maximum thickness to having the second maximum thickness, when bent to a maximum amount, a radius of curvature of the first segment is a first radius of curvature, when bent to a maximum amount, a radius of curvature of the third segment is a second radius of curvature, and the first radius of curvature is larger than the second radius of curvature.

18. An apparatus for tissue trigger point therapy, said apparatus comprising:

an elongated core comprising a bendable portion, a first end portion forming a first terminal end of the elongated core, and a second end portion forming a second terminal end of the elongated core; and an outer covering member that at least partially surrounds the elongated core and that is also bendable with the bendable portion of the elongated core, wherein:

the bendable portion of the elongated core is bendable in response to an applied bending force that at least meets a threshold amount of force being applied to the bendable portion, the bendable portion is comprised of a first gooseneck hose tube member and a second gooseneck hose tube member, the first gooseneck hose tube member having a first bending force threshold and the second gooseneck hose tube member having a second bending force threshold, such that different portions of the bendable portion have different bending force thresholds, application of the applied bending force to the bendable portion causes the apparatus to be bent into a bent shape, the apparatus is structured to retain the bent shape after the applied bending force is no longer applied to the bendable portion, the first end portion is disposed within the apparatus at a first region that is proximate to or overlapping with a first terminal end region of the apparatus, and the second end portion is disposed within the apparatus at a second region that is proximate to or overlapping with a second terminal end region of the apparatus, the first end portion and the second end portions are not bendable, resulting in the first and second regions also not being bendable, the apparatus is divisible into three different segments based on differences in diameter, the three different segments including a first segment, a second segment, and a third segment, the first segment has a first maximum thickness, the third segment has a second maximum thickness that is smaller than the first maximum thickness, the second segment is a transition segment that progressively transitions from having the first maximum thickness to having the second maximum thickness, and when the apparatus is straightened into an unbent shape, a combination of the bendable portion and the outer covering member is asymmetrical along a perpendicular, central axis positioned at a lengthwise center point of the apparatus, said combination being asymmetrical as a result of a progressive thickening of a portion of the outer covering member, and when the apparatus is straightened into the unbent shape, said combination has rotational symmetry along a central axis that extends along a length-wise direction of the apparatus.

19. An apparatus for tissue trigger point therapy, said apparatus comprising:

an elongated core comprising a bendable portion, a first end portion forming a first terminal end of the elongated core, and a second end portion forming a second terminal end of the elongated core; and an outer covering member that at least partially surrounds the elongated core and that is also bendable with the bendable portion of the elongated core, wherein:

the bendable portion of the elongated core is bendable in response to an applied bending force that at least meets a threshold amount of force being applied to the bendable portion, the threshold amount of force needed to bend the bendable portion is a value within a range spanning from 1 pound of force to 5 pounds of force, the bendable portion is comprised of a first gooseneck hose tube member and a second gooseneck hose tube member, the first gooseneck hose tube member having a first bending force threshold and the second gooseneck hose tube member having a second bending force threshold, such that different portions of the bendable portion have different bending force thresholds, application of the applied bending force to the bendable portion causes the apparatus to be bent into a bent shape, the apparatus is structured to retain the bent shape after the applied bending force is no longer applied to the bendable portion, the first end portion is disposed within the apparatus at a first region that is proximate to or overlapping with a first terminal end region of the apparatus, and the second end portion is disposed within the apparatus at a second region that is proximate to or overlapping with a second terminal end region of the apparatus, the first end portion and the second end portions are not bendable, resulting in the first and second regions also not being bendable, when the apparatus is straightened into an unbent shape, a combination of the bendable portion and the outer covering member is asymmetrical along a perpendicular, central axis positioned at a length-wise center point of the apparatus, said combination being asymmetrical as a result of a progressive thickening of a portion of the outer covering member, and when the apparatus is straightened into the unbent shape, said combination has rotational symmetry along a central axis that extends along a length-wise direction of the apparatus.

* * * * *